United States Patent
Hornung et al.

(10) Patent No.: US 8,353,891 B2
(45) Date of Patent: Jan. 15, 2013

(54) ABSORBENT INCONTINENCE ARTICLE

(75) Inventors: Fridmann Hornung, Penalolén Santiago (CL); Ruediger Kesselmeier, Herbrechtingen (DE); Enno Gause, Heidenheim (DE); Andreas Boehmler, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 517 days.

(21) Appl. No.: 12/311,853

(22) PCT Filed: Apr. 27, 2007

(86) PCT No.: PCT/EP2007/003733
§ 371 (c)(1), (2), (4) Date: Apr. 16, 2009

(87) PCT Pub. No.: WO2008/049468
PCT Pub. Date: May 2, 2008

(65) Prior Publication Data
US 2010/0318055 A1 Dec. 16, 2010

(30) Foreign Application Priority Data
Oct. 23, 2006 (DE) .................. 10 2006 050 971

(51) Int. Cl.
*A61F 13/15* (2006.01)
(52) U.S. Cl. ....... 604/385.31; 604/385.201; 604/385.01; 604/392

(58) Field of Classification Search ............ 604/385.31, 604/385.201, 385.03, 385.01, 392
See application file for complete search history.

(56) References Cited

U.S. PATENT DOCUMENTS
3,616,114 A 10/1971 Hamaguchi
(Continued)

FOREIGN PATENT DOCUMENTS
DE 102 21 597 11/2002
(Continued)

*Primary Examiner* — Lynne Anderson
(74) *Attorney, Agent, or Firm* — Paul Vincent

(57) ABSTRACT

An absorbent incontinence article (2) has a main part (4) composed of a front area (6) and of a rear area (8) and, lying between these in the longitudinal direction (10), a crotch area (12) that comes to lie between the legs of a user, the main part (4) comprising an absorption body (14), and with mutually separate side portions (16) which are joined to the rear area (8) and/or to the front area (6) on both sides and which extend in the transverse direction (22) across lateral longitudinal edges (20) of the main part (4) and connect the front area (6) and the rear area (8) to each other when the article is applied. To prevent tearing of the side portions, it is proposed that the incontinence article be designed such that the side portions (16) have a reinforcing means (24) which, seen in the transverse direction (22), is designed narrower than a respective side portion (16), and which is provided at least in an area bridging the longitudinal edge (20) of the main part (4), that is to say crosses both a lateral longitudinal edge area of the main part (4) and also a part of the side portion (16) in the transverse direction (22).

13 Claims, 6 Drawing Sheets

U.S. PATENT DOCUMENTS

| | | | |
|---|---|---|---|
| 3,848,594 A | 11/1974 | Buell | |
| 4,055,182 A | 10/1977 | Mack | |
| 4,209,016 A | 6/1980 | Schaar | |
| 5,695,488 A * | 12/1997 | Sosalla | 604/385.24 |
| 5,899,895 A | 5/1999 | Robles | |
| 6,197,012 B1 | 3/2001 | Mishima | |
| 7,527,618 B2 * | 5/2009 | Benning et al. | 604/392 |
| 7,947,028 B2 * | 5/2011 | Cohen et al. | 604/385.09 |
| 2003/0065295 A1 * | 4/2003 | Malchow et al. | 604/365 |
| 2004/0082931 A1 | 4/2004 | Tani | |
| 2004/0158224 A1 | 8/2004 | Kline | |
| 2006/0089616 A1 | 4/2006 | Belau | |
| 2006/0129121 A1 | 6/2006 | Erdman | |

FOREIGN PATENT DOCUMENTS

| | | |
|---|---|---|
| DE | 698 18 743 | 4/2004 |
| DE | 10 2004 021 353 | 11/2005 |
| DE | 601 17 462 | 10/2006 |
| JP | 09-508546 | 9/1997 |
| JP | 2001-157692 | 6/2001 |
| WO | WO 2005/102241 | 11/2005 |

* cited by examiner

ABSORBENT INCONTINENCE ARTICLE

This application is the national stage of PCT/EP2007/003733 filed on Apr. 27, 2007 and claims Paris Convention Priority to DE 10 2006 050 971.4 filed Oct. 23, 2006.

BACKGROUND OF THE INVENTION

The invention relates to an absorbent incontinence article with a main part composed of a front area and of a rear area and, lying between these in the longitudinal direction, a crotch area that comes to lie between the legs of a user, the main part comprising an absorption body, and with mutually separate side portions which are joined to the rear area and/or to the front area on both sides and which extend in the transverse direction across lateral longitudinal edges of the main part and connect the front area and the rear area to each other when the article is applied.

Such incontinence articles are known and described, for example in WO 2005/102241 A1. The side portions, sometimes also termed ears, are preferably attached directly to the main part, the chassis of the hygiene article, by a cut & place method. This production technology makes it possible to manufacture the side portions from a different raw material from the central main part of the hygiene article. For example, the side portions could be made permeable to air while the central main part is constituted so as to be essentially impermeable to moisture.

From the production point of view, the most efficient, simplest, and lowest-cost shape of the side portions is rectangular. During production, this permits conveyance of the material constituting the side portions as a continuous web of flat material, from which the side portions are then separated in the transverse direction relative to the machine direction. There is practically no waste from off-cuts. However, it is possible for the side portions to have any contour, that is, in particular, to be oblique or curved relative to the longitudinal or transverse direction of the hygiene article. However, this would result in costly waste from off-cuts, at least, if the side portions were separated, positioned, and attached directly by the cut & place method.

However, it has been shown that, in particular, if the side portions have the otherwise advantageous rectangular shape, the problem sometimes occurs that, when the hygiene article is applied and worn, the attached side portions can tear in the region of the lateral longitudinal edges of the main part. It has been shown that, when applying the hygiene article, users tend to exert a tensile force on the side portions that is oblique to the transverse and longitudinal direction of the hygiene article, which is indicated in FIG. 2a by an oblique upward-pointing arrow. In such cases, the side portions may tear along the lateral longitudinal edges of the main part, the tear starting from the transverse edge of the side portion facing the crotch area. Until now, attempts were made to improve the attachment of such side portions to the main part of hygiene articles by an optimized joining pattern, according to WO 2004/017882 A2 and WO 02/17843 A2.

The object of this invention is to solve the problem described above even more effectively, that is, to create absorbent incontinence articles having at least two laterally attached and joined side portions, which significantly improve the tearing behavior of the side portions.

SUMMARY OF THE INVENTION

This object is inventively achieved on an absorbent incontinence article of the type stated above by providing the side portions with a reinforcing means which, seen in the transverse direction, is designed narrower than a respective side portion, and which is provided at least in an area bridging the longitudinal edge of the main part, that is to say crosses both a lateral longitudinal edge area of the main part and also a part of the side portion in the transverse direction.

For the first time, the inventive suggestion optimizes not only the direct overlap region of each side portion with the main part where the joining connection is provided between the side portion and the main part but a reinforcement is provided in a region crossing the longitudinal edge of the main part. The reinforcement therefore extends beyond the longitudinal edge of the main part toward a further transverse extent of the side portion. This considerably increases the tear resistance of the side portions.

It proves especially advantageous if the reinforcing means essentially extends at least almost to a transverse edge of the side portion facing the crotch area, that is, if it is flush at the edges with the transverse edge of the side portion, or includes or surrounds the transverse edge, or extends beyond the transverse edge.

The reinforcing means could extend in the longitudinal direction of the hygiene article, for example, over the entire longitudinal extent of the attached side portion. It has since been shown that this is not absolutely necessary but that it is also advantageous if the reinforcing means in the longitudinal direction of the hygiene article have a smaller dimension than the attached side portion. As a consequence of the forces exerted on the side portion and on the joining region of the side portion and main part of the diaper during use discussed above, it is sufficient for the reinforcing means to extend, for example, only up to 80% or, in particular, up to 60% and further, in particular, up to 50% of the longitudinal extent of the side part. This can save material as compared with continuous reinforcement in the longitudinal direction.

The reinforcing means always extends in the transverse direction beyond the longitudinal edge of the main part toward the free end of the side portion. This extent of the region protruding beyond the longitudinal edge of the main part toward the free end of the side portion is, measured from the lateral longitudinal edges, preferably no more than 50%, further, preferably no more than 30%, in particular, no more than 25%, further, in particular, no more than 20%, further, in particular, no more than 15%, further in particular, no more than 10% of the transverse extent of the side part.

It proves especially advantageous that each attached side portion can be formed in a rectangular shape without the problem of tearing mentioned above arising as a result.

According to a first embodiment of the invention, the inventive reinforcing means can be advantageously constituted by an attached reinforcing portion, that is, by material additionally added to the respective side portion in each case, in particular, attached on the side portion in each case. This reinforcing portion can, for example, be constituted in the shape of a strip. This reinforcing portion can furthermore have any shape. This reinforcing portion can, for example, also be constituted in the shape of a triangle.

It could be a portion made of a strip- or ribbon-shaped material. In particular and advantageously, the reinforcing portion can be constituted by a nonwoven material, a textile material, or a foil. It can also, just like the side portions, be fed and attached in a continuous production process by the cut & place method.

Multiple reinforcing portions can also be provided. The reinforcing means can be attached to one or both top sides of the side portion.

The reinforcing portion is preferably constituted by a nonwoven, in particular and preferably, spunbond materials (S) or spunbond meltblown materials (SM), or meltblown layers (SMS) fitted on both sides with spunbond materials. Carded nonwoven materials can also be used. A polypropylene (PP) spunbonded nonwoven (spunbond material) with a mass per unit area of 20 to 35 g/m², in particular, 20 to 30 g/m² has proven advantageous. Also nonwoven laminates, that is, in particular, two-layer, three-layer, or multiple-layer combinations can be used. If the reinforcing portion is made from a foil, it is suggested, in particular, that this foil be constituted such that it is permeable.

This reinforcing means is advantageously attached by gluing, thermal welding, ultrasonic welding, needle-punching, or sewing on one or both top sides of each side portion.

The reinforcing means can be attached by the afore-mentioned joining method at least in sections, further, in particular, over the full area on one or both top sides of each side portion.

In an especially advantageous embodiment of the invention, the reinforcing means is constituted by the material of the side portion itself, by folding the side portion into the region bridging the longitudinal edge of the main part once or multiply. In the top view onto the unfolded hygiene article according to this embodiment, a region of each side portion crossing or overlapping the longitudinal edge of the main part is constituted by doubling or multiply increasing the material by folding the side portion. This creates especially effective tear protection. A Z-shaped fold of each side portion in the longitudinal direction of the hygiene article proves especially advantageous.

The side portions attached to the main part have, in the region of the join to the main part, an extent in the longitudinal direction of the hygiene article of preferably at least 10 cm, in particular, at least 14 cm, in particular, at least 18 cm and further, in particular, at least 22 cm.

The extent of a side portion attached to the main part in the unfolded state in the transverse direction beyond the longitudinal edge of the main part is at least 5 cm, in particular, at least 10 cm, in particular, at least 15 cm, and further in particular, at least 18 cm. This extent is preferably no more than 50 cm, preferably no more than 35 cm, in particular no more than 30 cm and further, in particular no more than 27 cm.

The overlap region of each side portion with the main part extends in the transverse direction preferably at least 0.5 cm, further preferably at least 1.5 cm, further preferably at least 2.0 cm, further, in particular at least 2.5 cm, further, in particular no more than 4.0 cm and further, in particular further no more than 3.5 cm.

The side portions are preferably connected in the overlap region with the material of the main part constituting the chassis, that is, in particular, the backsheet and/or the topsheet.

The side portions are preferably attached between the backsheet and topsheet.

The side portions attached to the main part are preferably constituted by a nonwoven, in particular and preferably, spunbond materials (S) or spunbond meltblown materials (SM), or meltblown layers (SMS) fitted on both sides with spunbond materials. Carded nonwoven materials can also be used. Nonwoven laminates, that is, in particular, two-layer, three-layer, or multiple-layer combinations of the afore-mentioned nonwovens can also be deployed.

The connection between the individual layers can be established by standard and known methods, for example, by thermal joining methods (welding, in particular, laser welding, air-through) or by ultrasonic welding methods; cold pressing, needle-punching, sewing, or gluing (for example by hotmelt) of nonwoven materials. Connection with textile fabrics or knitteds, that is, with materials constituted by a textile joint in the broadest sense of the term is also conceivable.

The side portions attached to the main part can also be constituted by a foil. If the intention is to make the side portion out of foil, it is proposed, in particular, that this foil be constituted such that is permeable to air.

The side portions attached to the main part can also be constituted as nonwoven-foil-laminate. If the intention is to make the side portion out of a nonwoven-foil-laminate, it is suggested, in particular, that the integrated foil be constituted such that it is permeable to air. The connection between the layers can be established by known joining methods, as explained above.

The side portions attached to the main part are preferably constituted, at least in sections, such that they are permeable to air, wherein, in particular, microporosity permitting both an exchange of air and permeability for moisture in the form of water vapor is regarded as advantageous. The side portions are preferably formed from a material that is permeable to water-based liquids. This accelerates the passage of perspiration from inside to outside.

The side portions advantageously have a mass per unit area of 10 to 150 g/m², in particular, 20 to 100 g/m², further, in particular 25 to 50 g/m².

It furthermore proves advantageous if regions of each side portion folded upon themselves are inseparably connected together in the bridging region of the longitudinal edge of the main part. In this case, this then forms the reinforcing means. For this purpose, any joining methods and joining means can be deployed. The use of adhesive materials is preferred due to their added reinforcing effect. The adhesive materials can be applied over the full area, in strips, in spots, or in a pattern. Hot-melt adhesive is preferred as the adhesive material.

Separately from the preceding improvement of the tear protection of attached side portions, it proves advantageous if regions of the side portions that are located in the transverse direction outside the longitudinal edge are folded upon themselves at least about a fold line extending in the longitudinal direction. This refers to regions of the side portions lying further out in the transverse direction. This fixes side portions that partially protrude far to the side—such as are found on incontinence articles—in this configuration during production in fast running processes to avoid unwanted flapping. It also presents an appealingly arranged appearance to the user immediately before use of the incontinence article.

In a further embodiment of this principle, the said partial portions of the side portions, which are folded upon one another and are contiguous over an area, are advantageously fixed to one another in this folded configuration such that they can be unfolded and separated. This is to provide a temporary separable fixture for the purpose of production and transportation until just before the article is used.

It also proves advantageous if each side portion folded in this manner comprises a grab area for unfolding the side portion and the separable fixture is separated by a single pull on the grab area of each side portion during unfolding.

The inventive absorbent hygiene article provides much improved protection against tearing of the side portions attached to the main part at both sides. The tear resistance in the transitional region from the main part to the side portion is, according to the test to be described, at least 35 N, in particular, at least 38 N, in particular, at least 40 N and further in particular, at least 42 N.

The stretch until the maximum tensile force ($F_{max}$) has been reached during the test to be described below is preferably at least 110%, in particular, at least 113%, in particular, at least 115%, in particular, at least 118%, in particular, at least 120% and further in particular, at least 122%.

Test for Determining the Tear Resistance:

The tear resistance is determined as the maximum force or the force during a stretch test using a tensile test device according to ISO 527-1 (1996). Such a tensile test device is sold by Zwick GmbH & Co. KG, Ulm, Germany. A specimen to be tested is clamped in the clamps of the said tensile test device (Zwick clamps with a dimension of 60 mm in the direction transverse to the pulling direction and 30 mm in the pulling direction). The clamping length (=distance of the clamps from the beginning of the tensile test) is 45 mm. A preliminary force of 0.2 N is exerted. Then measurement is started at a test velocity of a constant 500 mm/min and the tensile force between the clamps is measured and recorded. The positioning of the clamps on the specimen constituted by the incontinence article with the main part and side portions is explained in the description of the figures.

The number of test cycles should be n=10. As the tear resistance, the maximum force $F_{max}$ on each individual measurement is determined, that is, the peak force within the recorded force curve, and the mean value out of 10 measurements is then stated as the tear resistance. The peak force typically indicates the inception of tearing.

A further parameter that can be measured as part of conducting the test for determining the tear resistance is the stretch, measured as the distance between the clamps at $F_{max}$ in relation to the distance between the clamps at the beginning of the tensile test (=clamping length); it is stated as a percentage. In the case, too, the mean value out of 10 single measurements is taken.

Further characteristics, details, and advantages of the invention result from the appended claims and from the drawings and the following description of preferred embodiments of the inventive incontinence article. The drawings show:

BRIEF DESCRIPTION OF THE DRAWING

FIG. 3 a sectional view of an attachment region of a side portion on the main part as a schematic representation referring to intersecting plane III-III in FIG. 2a.

DESCRIPTION OF THE PREFERRED EMBODIMENT

Figure 1:
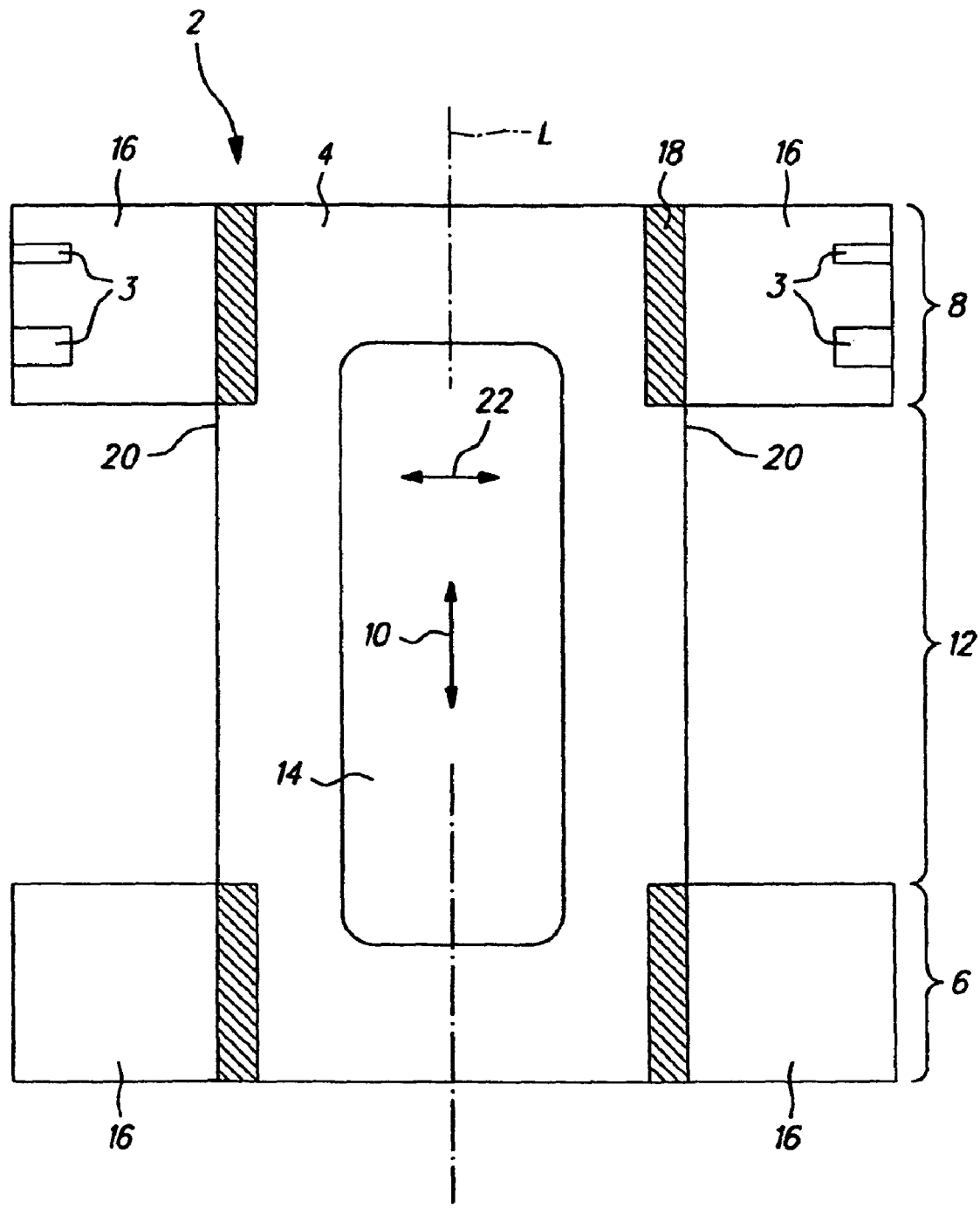
FIG. 1 a top view of an incontinence article as a schematic representation with side portions attached on both sides.

FIG. 1 schematically shows a top view of an absorbent incontinence article 2 in a condition of having just been unfolded. The incontinence article comprises the main part 4 with a longitudinal centerline L and composed of a front area 6, a rear area 8, and, lying between these in the longitudinal direction 10, crotch area 12. Also indicated is an absorbent body 14, which is usually disposed between the materials of the chassis, that is, in particular, between a permeable topsheet and a largely impermeable backsheet of the main part 4. However, embodiments are also possible in which the absorbent body can be applied and fixed to a chassis-forming layer of the main part as a separate unit provided with leakage protection.

The incontinence article 2 also comprises side portions 16, which are attached to the main part 4, in the case presented as an example, as separate pieces of material both in the front area 6 and in the rear area 8 on both sides. Each has a rectangular shape, which is not mandatory, but is advantageous with respect to avoiding wasteful off-cuts. The side portions are connected, inseparably during use as intended, in a hatched overlap region 18 with chassis-forming materials of the main part 4, that is, for example, with the backsheet and/or the topsheet. They extend beyond the lateral longitudinal edges 20 of the main part 4 in the transverse direction 22 of the main part 4 or of the incontinence article 2. The side portions 16 are designed and intended to be fastened to each other when the incontinence article is applied to form a hip area of the hygiene article that is continuous in the circumferential direction. The side portions are connected to each other on each side of the main part. It is also possible, for example, for side portions 16 to be provided only in the rear area 8, which are then fixed to the front area 6 of the main part 4 by means of the fastening elements 3.

Figure 2A:
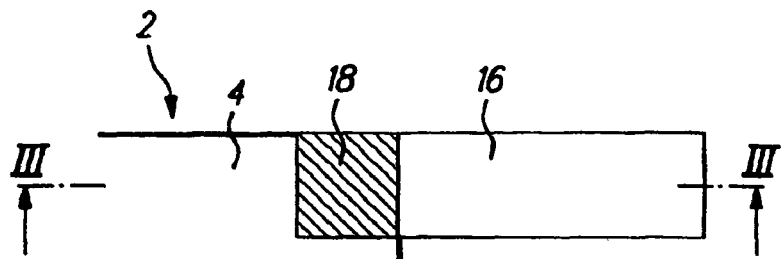
FIGS. 2a-e schematic representations of the attachment of the side portion to the main part (FIGS. b-e with different reinforcing means)

FIG. 2a shows another schematic representation of the attachment of one side portion 16 to a main part 4 of an incontinence article 2. Here again, an overlap region 18 of the side portion 16 and main part 4 is shown hatched, as is known and usual in the prior art.

Figure 2B:
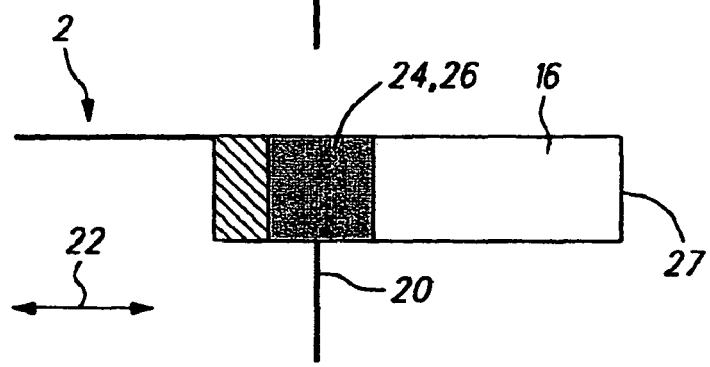

FIGS. 2b to e each show an inventive embodiment of the incontinence article 2, wherein the schematically shown side portion 16 comprises a reinforcing means 24 that is narrower in the transverse direction 22 than the side portion 16. The reinforcing means 24, however, extends in the transverse direction 22 beyond the longitudinal edge 20 of the main part 4. The reinforcing means 24 partially bridges the overlap region 18, as is schematically shown in FIG. 2b. It extends both over the lateral longitudinal edge 20 toward the free end 27 of the side portion 16 and also toward the overlap region 18, that is, toward a longitudinal centerline L of the main part 4.

The reinforcing means 24 can be constituted in different ways as long as it provides tear protection of the side portion 16, in particular, when a tensile force directed obliquely with respect to the transverse direction 22 is exerted on the side portion 16 or on the overlap region 18. The reinforcing means 24 can, for example, be constituted by an additional reinforcement portion 26, for example, made of nonwoven or foil, or of any reinforcing material. This can be applied to the material of the side portion 16 by any attachment method, in particular, using an adhesive.

Figure 2C:
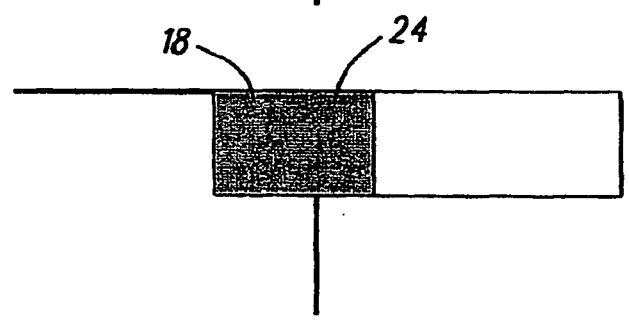

In the embodiment according to FIG. 2c, the reinforcing means 24 crosses the entire overlap region 18 in the transverse direction 22.

Figure 2D:
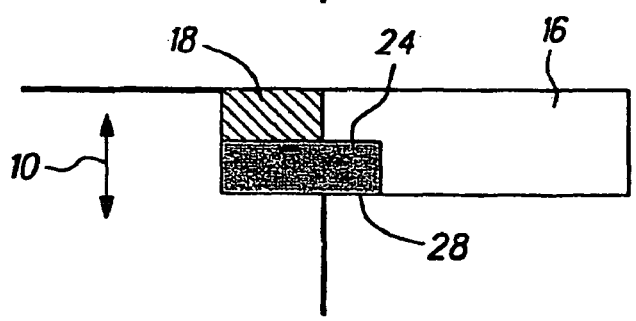
Figure 2E:
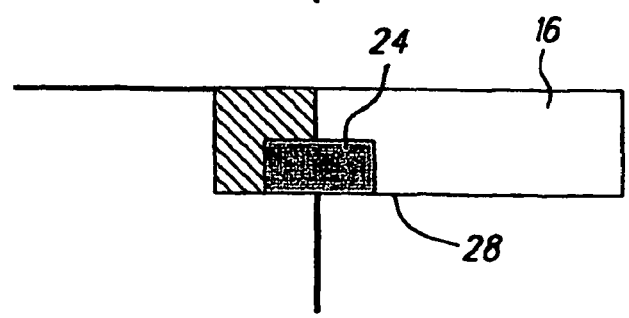

In the embodiment according to FIG. 2d, the reinforcing means 24 extends in the longitudinal direction 10 from a transverse edge 28 of the side portion 16 facing the crotch area only up to half of the longitudinal extent of the side portion 16. This has proved sufficient for the provision of effective tear protection. The embodiment shown in FIG. 2e is similar to that in FIG. 2b, wherein the reinforcing means 24 again extends only up to half of the longitudinal extent of the side portion 16 starting from the transverse edge 28 facing the crotch area. In all inventive embodiments according to FIGS. 2b-e, tearing starting from the transverse edge 28 facing the crotch area along the longitudinal edge 20 of the main part 4 is prevented.

Figure 3:
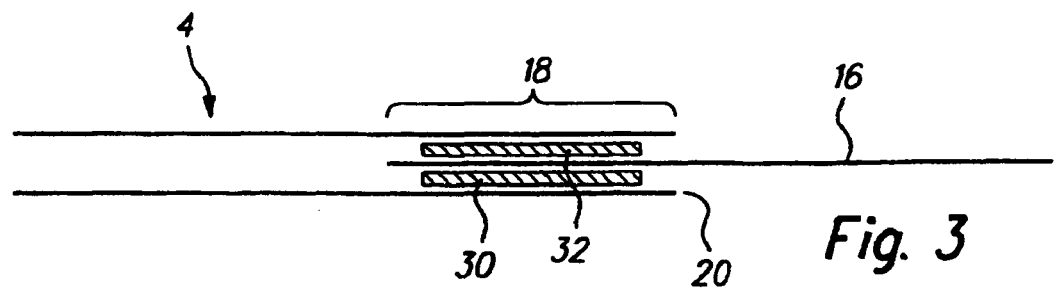
Figure 4:
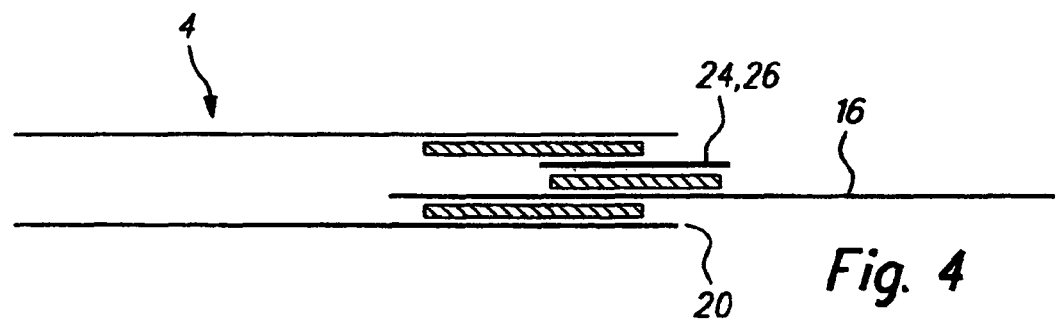
FIGS. 4-6 sectional views of different embodiments of the inventive attachment of the side portions to the main part referring to the same intersecting plane as in FIG. 3

FIG. 3 shows a sectional view of an example of a known embodiment of the attachment of a side portion to the main part, referring to intersecting plane III-III in FIG. 2a. In an overlap region 18, the side portion 16 extends between two layers, for example, between a topsheet and backsheet of the main part 4 of a hygiene article. In this overlap region 18, the side portion 16 is inseparably connected to the chassis materials by means of a first and second layer of adhesive 30, 32. Especially in this embodiment, there is a danger of tearing in the vicinity of a lateral longitudinal edge 20 of the main part 4. FIG. 4, for example, shows the inventive embodiment indicated in FIG. 2b, in which a reinforcing means 24 is provided in the form of a reinforcing portion 26 in such a way that it extends over the longitudinal edge 20 of the main part 4 in the transverse direction 22 starting from an overlap region 18.

Figure 5:
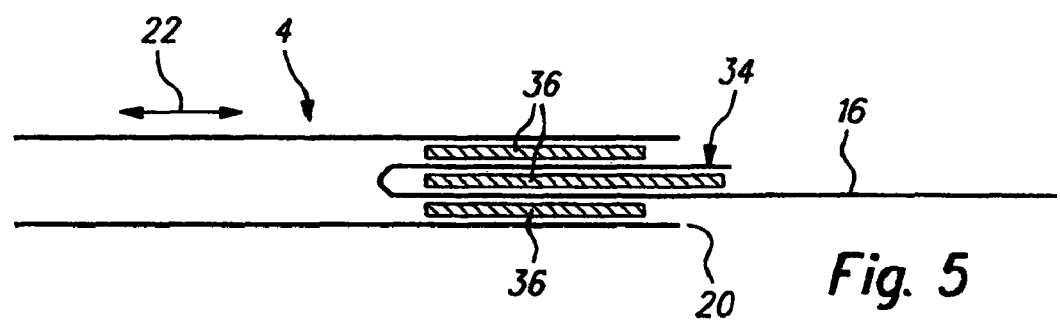
Figure 6:
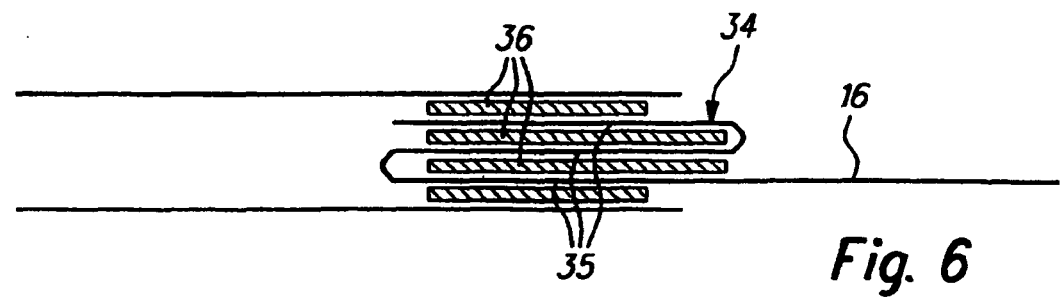

FIG. 5 shows a further inventive embodiment wherein the reinforcing means 24 is itself constituted by the material of the side portion 16 by folding the side portion 16 onto itself, wherein the folded configuration 34 extends in the transverse direction 22 beyond the longitudinal edge 20 of the main part 4. In the embodiment according to FIG. 6, the folded configuration 34 comprises a Z-shaped fold of the side portion 16. The folded areas 35 of the folded configuration 34 are inseparably joined together, for example, by means of adhesive materials 36 applied over an area or in spots.

Figure 7:
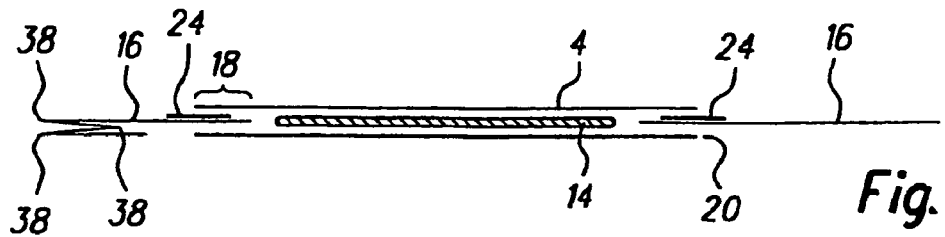
FIGS. 7 and 8 schematic sectional views of an incontinence article with folded side portions.
Figure 8:
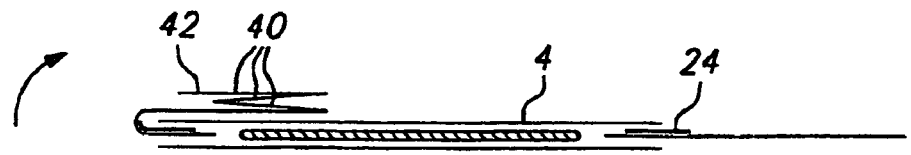

FIGS. 7 and 8 show not only the reinforcing means 24 that crosses the longitudinal edge 20 of the main part 4 of the hygiene article but also that the side portions 16 outside of this reinforcing means 24 are folded upon themselves around multiple, in the illustrated case around three fold lines 38, extending in the longitudinal direction 10. The partial portions 40 that are thus folded upon one another and are contiguous over an area are preferably fixed to one another in such a way that they can be unfolded and separated. For example, ultrasonic welding points or other separable joining connections could be provided for this purpose. This separable fixture of the partial portions 40 to each other prevents the side portions 16 from flapping while being handled in fast running production machines.

FIG. 8 shows the folded configuration of the partial portions 40 folded inward, that is, onto the top side of the main part 4. It can be seen that the top partial portion 40 in FIG. 8 protrudes outwardly beyond the Z-shaped folded configuration and thus forms a grab area 42 for unfolding the side portion 16. This separable fixture of the partial portions 40 folded upon each other is preferably such that, on unfolding by a single pull on the grab area 42 in the transverse direction 22, the fixture is separated and the side portions are fully unfolded, that is, can be put into the configuration shown in FIG. 1.

Determining the Tear Resistance

Figure 9:
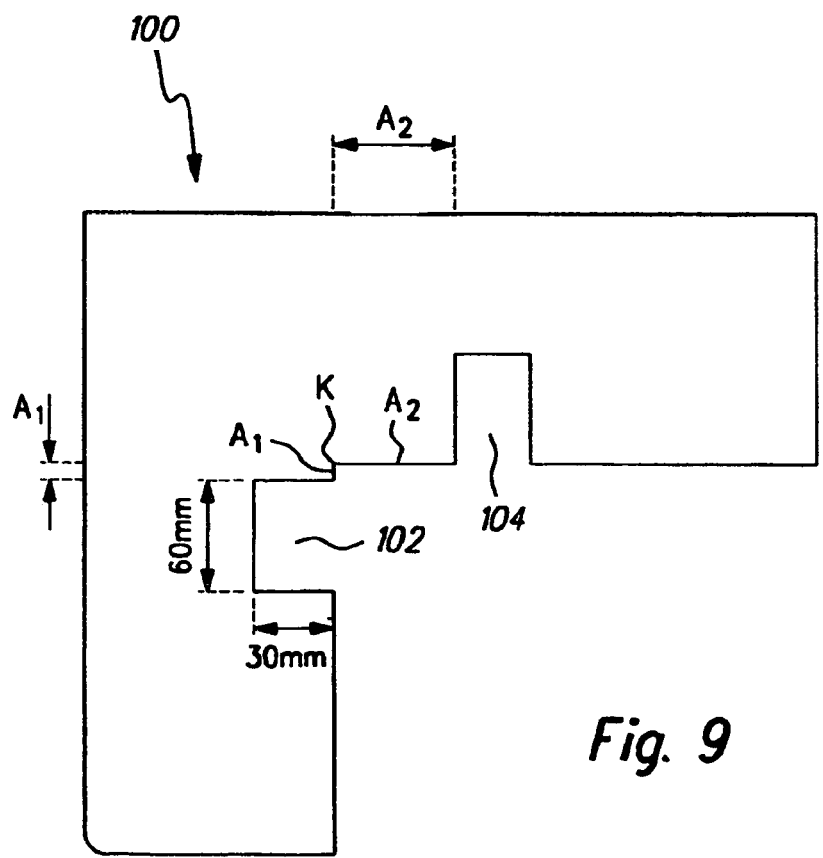
FIGS. 9 and 10 schematic view of a template for marking the configuration of the clamps for determining the tear resistance FIGS. 11a and 11b schematic view of the configuration of the specimen for determining tear resistance

A template 100 (shown in the top view in FIG. 9) whose cutouts 102, 104 reflect the configuration of the clamps 106, 108 of the tensile test device when the incontinence article to be tested is clamped is initially used to determine the tear resistance according to the test described above. The dimension $A_1$ of the template from the corner point K to the cutout 102 is 10 mm, and the dimension $A_2$ from the corner point K to the cutout 104 is 65 mm. As mentioned above, the dimensions of the cutouts 102, 104 are 30 mm and 60 mm and correspond to the dimensions of clamps 106, 108 of the tensile test device.

Figure 10:
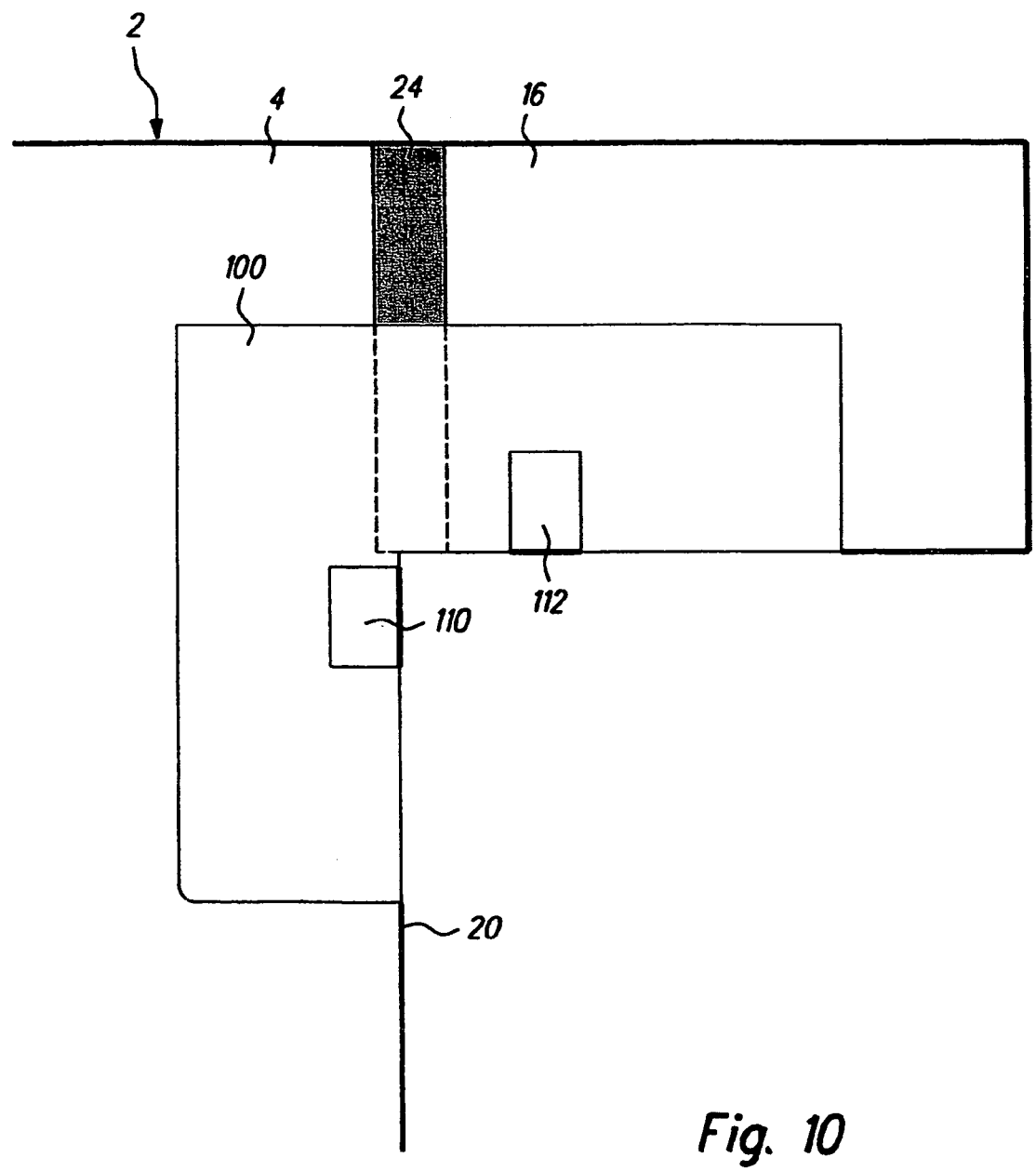

FIG. 10 illustrates how the clamps 106, 108 are fixed to the incontinence article 2 with the aid of template 100. FIG. 10 also shows the reinforcing means 24 that, in the example shown, extends in the longitudinal direction 10 over the entire longitudinal extent of the side portion 16 in the attachment area on the main part 4. For conducting the test, it is important that the reinforcing means 24 is not held by the clamps 106, 108. This can be achieved by using template 100, which also simulates an oblique tensile force on the transitional area. By applying template 100 which is oriented as shown in FIG. 10 with respect to the longitudinal edge 20 of the main part 4 and with respect to the transverse edge of the side portion 16, the clamping area 110, 112 on the incontinence article is determined by positioning and pulling tight the clamps 106, 108 of the tensile test device.

Figure 11A:
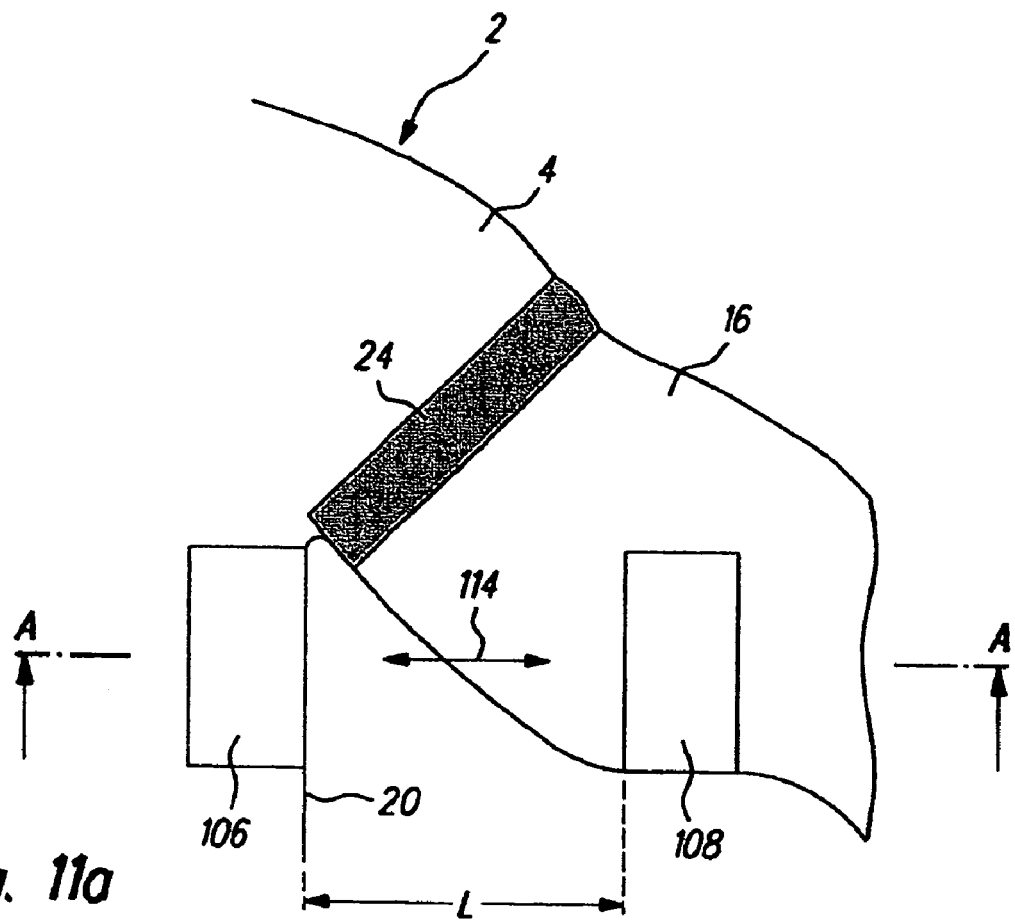
Figure 11B:
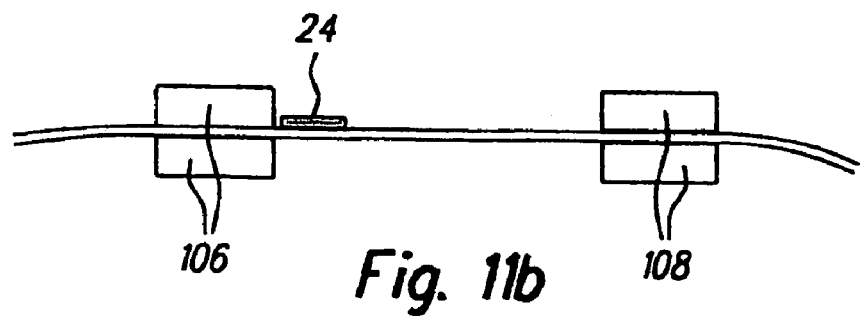

The tensile test is conducted with the clamps 106, 108 configured as shown in FIG. 11, wherein the reference symbol 114 denotes the direction of the relative movement of the clamps 106, 108. As already mentioned, the test starts with a clamping length L of 45 mm, the clamp 106 being stationary and the moving clamp 108 being pulled away in direction 114 at a test velocity of 500 mm/min. FIG. 11b shows a schematic sectional view of the configuration during the tensile test referring to the intersecting plane A-A in FIG. 11a.

The following tables 1 and 2 show the result of the measurement of an inventively constituted incontinence article (column "with reinforcement") compared with an incontinence article without reinforcing means (column "without reinforcement") that is otherwise identically constituted. In the case of the inventive incontinence articles, the reinforcing means used are a reinforcing portion made from a polypropylene spunbonded nonwoven with a mass per unit area of 30 g/m$^2$, which extends, according to the embodiment shown in FIG. 2c, over the entire longitudinal direction 10 of the side portion and in the transverse direction 22 as far as the inner longitudinal edge of the side portion. The overlap over the longitudinal edge 20 of the main part 4 was 2.5 cm inward and 1.5 cm outward.

Tables 1 and 2 show not only the peak forces $F_{max}$ but also the stretch when the peak force is reached as a percentage with reference to the clamping length with the mean value, standard deviation, and minimum and maximum measured values stated in each case.

It can be seen that the tear resistance as a mean value of 10 single measurements with 41.54 N or as a mean value of 10 single measurements with 47.56 N is very much higher than on the reference product with 26.51 N and 31.45 N respectively.

Moreover, the stretch at 115.08% and 136.92% is clearly greater than the stretch of 103.45% and 104.23% respectively.

TABLE 1

| No. | F-max [N] with reinforcement | F-max [N] without reinforcement | Stretch up to F-max [%] with reinforcement | Stretch up to F-max [%] without reinforcement |
|---|---|---|---|---|
| 1 | 39.59 | 20.07 | 116.61 | 102.55 |
| 2 | 43.00 | 27.21 | 118.63 | 95.90 |
| 3 | 41.32 | 33.27 | 108.47 | 119.18 |
| 4 | 35.14 | 26.98 | 91.71 | 88.95 |
| 5 | 37.36 | 31.12 | 115.04 | 97.25 |
| 6 | 34.89 | 25.82 | 101.36 | 122.44 |
| 7 | 43.63 | 24.39 | 119.88 | 96.40 |

TABLE 1-continued

| No. | F-max [N] with reinforcement | F-max [N] without reinforcement | Stretch up to F-max [%] with reinforcement | Stretch up to F-max [%] without reinforcement |
|---|---|---|---|---|
| 8 | 49.62 | 20.94 | 117.33 | 64.96 |
| 9 | 41.30 | 24.62 | 128.00 | 90.46 |
| 10 | 49.53 | 29.72 | 133.81 | 156.51 |
| Mean value | 41.54 | 26.41 | 115.08 | 103.46 |
| s | 5.19 | 4.20 | 12.20 | 24.56 |
| min | 34.89 | 20.07 | 91.71 | 64.96 |
| max | 49.62 | 33.27 | 133.81 | 156.51 |

TABLE 2

| No. | F-max [N] with reinforcement | F-max [N] without reinforcement | Stretch up to F-max [%] with reinforcement | Stretch up to F-max [%] without reinforcement |
|---|---|---|---|---|
| 1 | 48.17 | 36.38 | 175.17 | 102.81 |
| 2 | 44.20 | 34.98 | 122.58 | 122.75 |
| 3 | 46.41 | 31.46 | 139.51 | 101.73 |
| 4 | 50.58 | 27.02 | 156.46 | 98.58 |
| 5 | 47.62 | 29.53 | 140.68 | 99.34 |
| 6 | 43.89 | 36.15 | 108.45 | 112.07 |
| 7 | 51.64 | 32.12 | 144.84 | 97.76 |
| 8 | 51.05 | 27.66 | 149.09 | 103.76 |
| 9 | 48.23 | 32.89 | 118.85 | 103.75 |
| 10 | 43.84 | 26.33 | 113.60 | 99.79 |
| Mean value | 47.56 | 31.45 | 136.92 | 104.23 |
| s | 2.96 | 3.73 | 20.98 | 7.68 |
| min | 43.84 | 26.33 | 108.45 | 97.76 |
| max | 51.61 | 36.38 | 175.17 | 122.75 |

We claim:

1. An absorbent incontinence article comprising:
    a main part having a front area, a rear area and a crotch area disposed between said front area and said rear area in a longitudinal direction of the article, said crotch area structured, disposed and dimensioned to seat between legs of a user, said main part also having an absorption body;
    mutually separate, rectangular side portions, each rectangular side portion permanently joined to a chassis component of said main part in a region of overlap between said rectangular side portion and said chassis component, thereby fastening said rectangular side portions to said rear area and/or to said front area on both sides thereof to extend in a transverse direction across lateral longitudinal edges of said main part for connecting said front area and said rear area to each other when the article is applied; and
    reinforcing means cooperating with said main part and said side portions at said region of overlap, wherein said reinforcing means are attached, throughout an entire area thereof, to said main part and said side portions, said reinforcing means being narrower, in said transverse direction, than a respective said side portion and disposed at least in an area bridging said longitudinal edge of said main part, thereby crossing, in said transverse direction, both a lateral longitudinal edge area of said main part as well as a part of said side portion, wherein said reinforcing means substantially extends as far as a transverse edge of said side portion facing said crotch area or extends beyond said transverse edge, said reinforcing means also extending in an outwardly transverse direction from said region of overlap and past said lateral longitudinal edges of said main part.

2. The incontinence article of claim 1, wherein said reinforcing means has a smaller dimension in said longitudinal direction of the article than said side portion.

3. The incontinence article of claim 1, wherein said reinforcing means is constituted by an attached reinforcing portion.

4. The incontinence article of claim 3, wherein said attached reinforcing portion is in a shape of a strip.

5. The incontinence article of claim 3, wherein said attached reinforcing portion is constituted by a nonwoven material, a textile material, or a foil.

6. The incontinence article of claim 1, wherein said reinforcing means is attached by gluing, thermal welding, ultrasonic welding, needle-punching, or sewing on one or both topsides of said side portion.

7. The incontinence article of claim 1, wherein said reinforcing means is constituted by a material of said side portion itself, with said side portion being folded once or multiply in a region bridging said longitudinal edge of said main part, wherein regions of said side portion folded upon themselves are permanently connected to each other.

8. The incontinence article of claim 7, wherein said reinforcing means is constituted by a material of said side portion itself, with said side portion being folded in a shape of a Z in a region bridging said longitudinal edge of said main part, wherein regions of said side portion folded upon themselves are permanently connected to each other.

9. The incontinence article of claim 1, wherein regions of said side portions that lie in a transverse direction outside said longitudinal edge are folded upon themselves about at least one fold line extending in said longitudinal direction.

10. The incontinence article of claim 9, wherein partial portions of said side portions folded upon themselves and contiguous over an area are fixed to one another in a folded configuration in such a way that they can be unfolded and separated.

11. The incontinence article of claim 9, wherein each folded side portion comprises a grab area for unfolding said side portion, wherein a separable fixture on unfolding is separated by a single pull of said grab area of each of said side portions.

12. The incontinence article of claim 1, wherein a tear resistance in a transitional area between said main part and said side portion is at least 35 N.

13. The incontinence article of claim 1, wherein a stretch during performance of a test to determine a tear resistance until reaching a maximum tensile force is at least 110%.

* * * * *